United States Patent [19]
Matsuno et al.

[11] Patent Number: 5,039,863
[45] Date of Patent: Aug. 13, 1991

[54] AUTOMATIC RADIOISOTOPE FILLING APPARATUS

[75] Inventors: Masao Matsuno; Masaaki Tanaka, both of Ichihara; Satoshi Matsunami, Tokyo, all of Japan

[73] Assignee: Ube Industries, Ltd., Ube, Japan

[21] Appl. No.: 434,751

[22] Filed: Nov. 13, 1989

[30] Foreign Application Priority Data

| Nov. 15, 1988 | [JP] | Japan | 63-286645 |
| Nov. 15, 1988 | [JP] | Japan | 63-286646 |
| Nov. 15, 1988 | [JP] | Japan | 63-288028 |
| Nov. 15, 1988 | [JP] | Japan | 63-288029 |

[51] Int. Cl.$^5$ .......................................... G01N 23/00
[52] U.S. Cl. ............................................. 250/432 PD
[58] Field of Search ............................. 250/432 PD

[56] References Cited

U.S. PATENT DOCUMENTS

| 3,997,784 | 12/1976 | Picunko et al. | 250/432 PD |
| 4,296,785 | 10/1981 | Vitello et al. | 250/432 PD |
| 4,409,488 | 10/1983 | King | 250/432 PD |
| 4,625,118 | 11/1986 | Kriwetz et al. | 250/432 PD |
| 4,853,546 | 8/1989 | Abe et al. | 250/432 PD |

FOREIGN PATENT DOCUMENTS

59-51400 3/1984 Japan .
60-259967 12/1985 Japan .
62-99242 6/1987 Japan .
62-139667 6/1987 Japan .

Primary Examiner—Bruce C. Anderson
Attorney, Agent, or Firm—Armstrong, Nikaido, Marmelstein, Kubovcik, & Murray

[57] ABSTRACT

The automatic radioisotope filling apparatus of the present invention is equipped with a radioisotope vial containing a radioisotope solution, a saline vial containing a physiological saline solution, a dilution vial to which a predetermined amount of the radioisotope solution and a predetermined amount of the physiological saline solution are to be transferred to prepare a diluted radioisotope solution, a radiation detector for measuring the radioactive intensity of the diluted radioisotope solution prepared in the dilution vial, and a plurality of label vials containing a drug to be labeled. With this apparatus, the radiation exposure which the operator undergoes can be reduced and a diluted radioisotope solution of precisely known radioactivity can be transferred to the label vials, by employing special methods in stirring the label vials, in sequentially transferring the diluted radioisotope solution to the label vials, and in transferring the radioisotope solution and the physiological saline solution to the dilution vial and the label vials.

10 Claims, 8 Drawing Sheets

MILKED QUANTITY

AUTOMATIC RADIOISOTOPE FILLING APPARATUS

BACKGROUND OF THE INVENTION AND RELATED ART STATEMENT

The present invention relates to an automatic radioisotope filling apparatus for reducing the radiation exposure which the operator of the apparatus undergoes.

A drug labeled with a radioisotope (hereinafter referred to as a RI) (this drug is hereinafter referred to as a labeled drug), when injected into a human body, is selectively collected in a particular tissue or internal organ of the body, depending upon the type of labeled drug. Examination of the condition by an appropriate detector makes it possible to obtain the physiological or pathophysiological information of the tissue or internal organ in question.

Many nuclides are used as RIs for labeling. Of them, technetium 99m (Tc-99m) is used the most. Tc-99m is a daughter nuclide of Mo-99 and has a short half life of 6 hours. Therefore, Tc 99m is obtained, when required, in a form of a RI solution containing Tc-99m, from an apparatus generally called a technegenerator (RI generator) which contains Mo-99 and its daughter nuclide, namely, Tc 99m and from which only Tc-99m can be taken out selectively. As a matter of course, the radioactive intensity per unit volume, i.e. specific radioactivity of the RI solution taken out from the technegenerator varies by the time period since the production of the technegenerator or by the producer. Accordingly, the specific radioactivity of the RI solution must be measured correctly in order to prepare a labeled drug of a desired amount. Further, it is necessary in some cases to dilute the RI solution with a physiological saline solution to adjust the specific radioactivity of the former to a desired level.

Preparation of a labeled drug has been manually conducted by measuring the radioactive intensity of a RI solution contained in a RI vial, separately measuring the amount of the RI solution visually in most cases, calculating the specific radioactivity of the solution from its radioactive intensity and amount both obtained above, transferring required amounts of the RI solution and a physiological saline solution to a vial containing a drug by means of a syringe or the like, and effecting stirring.

Such manual handling of RI has been defective in that the operator undergoes a large radiation exposure as a result of such an operation over a long period of time and may possibly have a serious hazard.

In order to improve the manual handling of RI and thereby to reduce the radiation exposure which the operator undergoes, the present applicant proposed an automatic RI filling apparatus which can solve the above problems (reference is made to U.S. Pat. No. 4,853,546.

This automatic RI filling apparatus comprises:
(a) a RI vial containing a RI solution,
(b) a saline vial containing a physiological saline solution,
(c) a dilution vial to which a predetermined amount of the RI solution and a predetermined amount of the physiological saline solution are to be transferred to prepare a diluted RI solution,
(d) a radiation detector for measuring the radioactive intensity of the diluted RI solution in the dilution vial, and
(e) a plurality of label vials containing a drug to be labeled, wherein the diluted RI solution prepared in the dilution vial is automatically transferred to the label vials containing a drug to prepare a labeled drug.

The automatic RI filling apparatus enabled the significant reduction of the accumulated radiation exposure which the operator undergoes during the preparation of a labeled drug.

In the above automatic RI filling apparatus, however, there is a problem that the operator may undergo radiation when the operator opens the opening of a vial shield containing a label vial to take out the label vial for exchange, etc., because the opening is directed upright. Further in the automatic RI filling apparatus, each label vial is stirred after the diluted RI solution has been transferred to all the label vials; therefore, in the label vial to which the diluted RI solution has been transferred at first, the mixing of the diluted RI solution and the drug solution is insufficient until the transfer of the diluted RI solution to the other label vials is completed and the stirring of all the label vials is started; as a result, there occurs a reduction in labeling efficiency.

Further in the automatic RI filling apparatus, the RI solution contained in the RI vial is produced ahead of time by a generator (e.g. technegenerator) which milks a RI (e.g. technetium) to produce a RI solution, and then transferred to the RI vial; this production of a RI solution is effected by means of a vacuum vial, and suction lasts until the vacuum in the vacuum vial disappears; as a result, the RI solution becomes surplus when labeling requires a small amount of the RI solution. In some cases, the operator quits the collection of the RI solution in the middle: this is done based mainly on the operator's intuition; consequently, the amount of the RI solution collected and the radioactivity of the RI solution differ from those required.

Hitherto, there has existed no such automatic RI filling apparatus that has a generator incorporated therein and can integrally effect milking of RI, metering of the resulting RI solution, transferring of the solution and labeling of drug with the solution.

The above mentioned automatic RI filling apparatus has been found to further have the following problem. When a solution is suction-transferred between the vials by a metering means (e.g. syringe) or when a solution in the tube is discharged, a small volume of the RI solution adheres to the front end of the syringe piston and, in the subsequent transferring operation, this RI solution causes mixing with the RI solution to be newly transferred. The solution transferred into the tube cannot be completely withdrawn from the tube. The solution remains in the tube in the form of droplets adhering to the inner wall of the tube. As a result of these inconveniences, it is impossible to transfer the RI solution to the dilution vial or each label vial in an amount of a precisely known radioactivity.

OBJECTS AND SUMMARY OF THE INVENTION

Hence, the object of the present invention lies in providing an automatic radioisotope filling apparatus which has solved the above mentioned problems of conventional automatic RI filling apparatuses.

According to the present invention, there is provided an automatic radioisotope filling apparatus (hereinafter referred to as the first filling apparatus) comprising:
a radioisotope vial containing a radioisotope solution, a saline vial containing a physiological saline solution, and a plurality of label vials containing a drug into which a predetermined amount of the radioisotope solution or the physiological saline solution is to be provided, wherein the opening of each vial shield accommodating each label vial is directed obliquely upward at the back side of the vial shield when the stirring of each label vial has been completed.

This apparatus may further comprise a dilution vial so that the RI solution and the physiological saline solution are transferred to the dilution vial to prepare a diluted RI solution and the diluted RI solution is transferred to each label vial to prepare a labeled drug.

According to the present invention, there is further provided an automatic radioisotope filling apparatus (hereinafter referred to as the second filling apparatus) comprising:

a radioisotope vial containing a radioisotope solution, a saline vial containing a physiological saline solution, a dilution vial into which a predetermined amount of the radioisotope solution and a predetermined amount of the physiological saline solution are provided to prepare a diluted radioisotope solution, a radiation detector for measuring the radioactive intensity of the solution in the dilution vial, and a plurality of label vials containing a drug to be labeled, wherein the diluted radioisotope solution prepared in the dilution vial is provided into each of the label vials containing a drug to prepare a labeled drug and wherein the first label vial is provided with a predetermined amount of the diluted radioisotope solution and immediately subjected to stirring and then the second label vial is subjected to the same procedure.

In this apparatus, "the first label vial is provided with the diluted RI solution and immediately subjected to stirring" means to effect stirring within 30 seconds after the provision with the diluted RI solution. It is known that when a drug is mixed with a RI and the mixture is allowed to stand in an insufficient mixing condition, the labeling efficiency of the drug is lower as the standing time increases. Therefore, it is preferable to effect stirring within 30 seconds after the provision with the diluted RI solution.

According to the present invention, there is further provided an automatic radioisotope filling apparatus (hereinafter referred to as the third filling apparatus) comprising:

a radioisotope generator for milking a radioisotope to produce a radioisotope solution, a saline vial containing a physiological saline solution, a plurality of label vials containing a drug into which a predetermined amount of the radioisotope solution or the physiological saline solution is to be provided, a metering means for withdrawing a predetermined amount of the radioisotope solution from the radioisotope generator by suction, a dilution vial into which a predetermined amount of the radioisotope solution and a predetermined amount of the physiological saline solution are provided to prepare a diluted radioisotope solution, and a radiation detector for measuring the radioactive intensity of the radioisotope solution transferred to the dilution vial, wherein the specific radioactivity of the radioisotope solution transferred to the dilution vial is calculated based on the volume of the radioisotope solution transferred to the dilution vial and the radioactive intensity of the radioisotope solution measured by the radiation detector.

According to the present invention, there is further provided an automatic radioisotope filling apparatus (hereinafter referred to as the fourth filling apparatus) comprising:

a radioisotope vial containing a radioisotope solution, or a radioisotope generator for milking a radioisotope to produce a radioisotope solution, a saline vial containing a physiological saline solution, a syringe for withdrawing a predetermined amount of the radioisotope solution or the physiological saline solution by suction, a dilution vial into which a measured amount of the radioisotope solution or a measured amount of the physiological saline solution is to be provided, a plurality of label vials containing a drug into which a predetermined amount of the radioisotope solution or a predetermined amount of the physiological saline solution is to be provided, and a tube connecting the syringe, the vials and the generator, wherein in discharging the solution remaining in the tube, air of an amount at least equivalent to the internal volume of the solution discharging section of the tube is sucked into the syringe and then the solution remaining in the tube is discharged using the air as a buffer material.

The above and other objects, features and advantages of the present invention will become apparent from the following description.

BRIEF DESCRIPTION OF THE DRAWINGS

FIGS. 11 (a), (b), (c) and (d) are views showing a method for sucking a solution into a syringe.

DETAILED DESCRIPTION OF A PREFERRED EMBODIMENT

The present invention is described in detail referring to embodiments shown in the accompanying drawings.

However, the present invention is in no way restricted to these embodiments.

Description is made firstly on the first filling apparatus.

Figure 1:
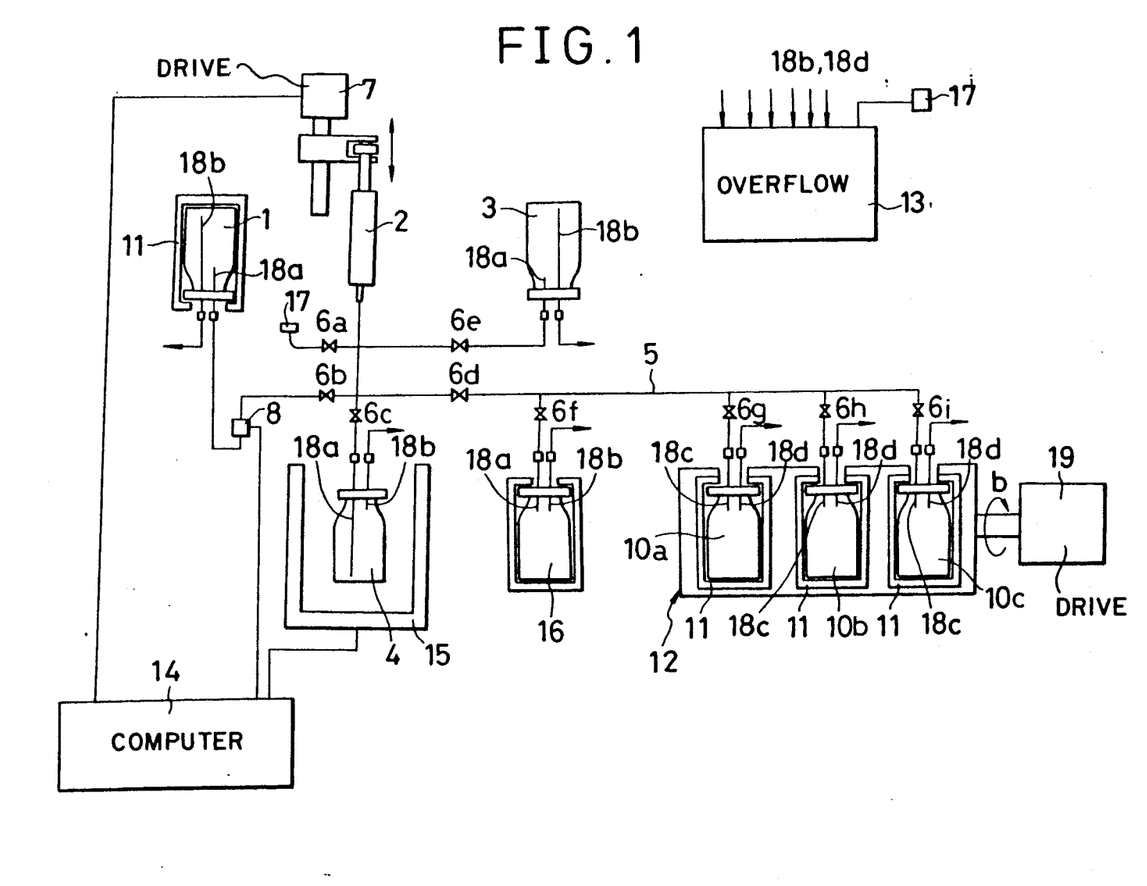
FIG. 1 is a schematic view showing one embodiment of the first filling apparatus of the present invention.
Figure 2:
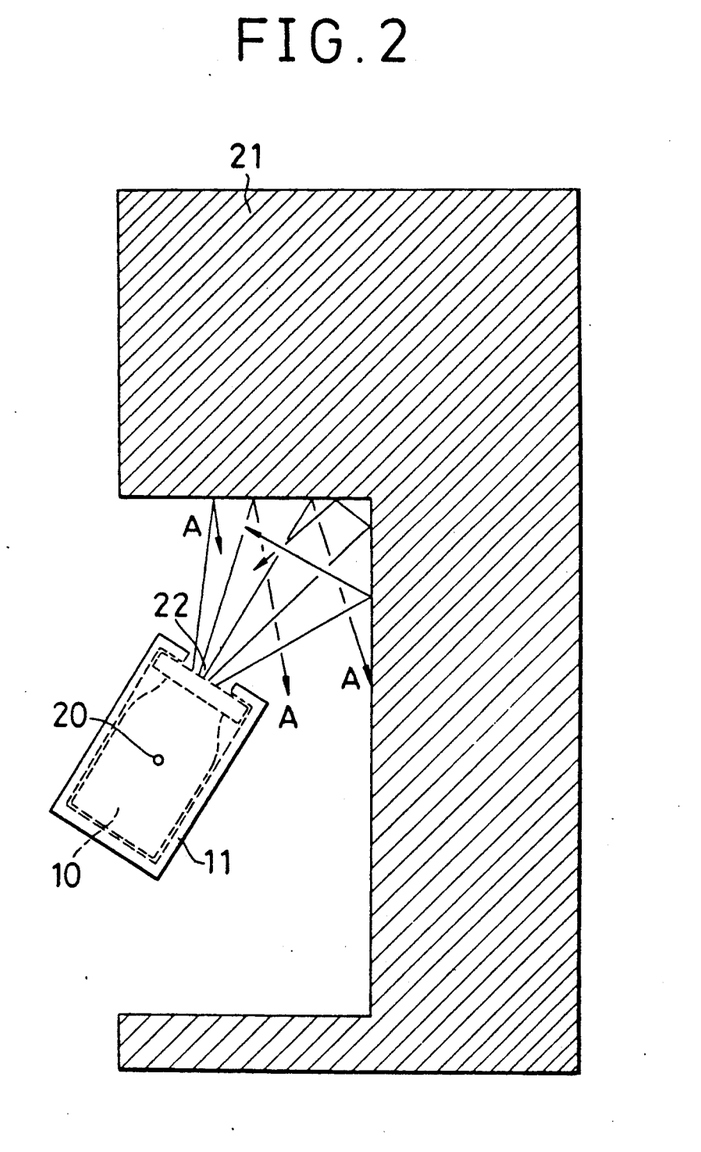
FIG. 2 is a view showing a state that a vial shield containing a label vial has come to a standstill after the completion of the stirring operation, with its opening directed obliquely upward at the back side (the side opposite to the operator).

FIG. 1 shows one embodiment of the first filling apparatus. FIG. 2 shows a state that a vial shield containing a label vial has come to a standstill after the completion of the stirring operation, with its opening directed obliquely upward at the side opposite to the operator.

A RI vial 1 containing a RI solution, a syringe 2, a saline vial 3 containing a physiological saline solution, a dilution vial 4, a drain vial 16 and a label vial 10 (a generic name of label vials 10a to 10c) are connected to each other by a tube 5 via injection needles 18a, 18b, 18c and 18d. Switching valves 6a to 6i are provided in the middle of the tube 5 and are opened or closed by a command from a computer 14.

In the syringe 2, its piston makes a vertical movement controlled by a driving device 7 operating in accordance with a command from the computer 14 and thereby performs the collection and transfer of a solution.

One injection needle 18a for collection or transfer of a solution and one injection needle 18b for degassing are inserted into the RI vial 1, the saline vial 3, the dilution vial 4 and the drain vial 16 at their rubber stopper portions. The injection needles 18a are connected to an overflow bag 13 and then communicated to the atmosphere via a filter 17. One injection needle 18c for transfer of a diluted RI solution and one injection needle 18d for degassing are inserted into the label vial at its rubber stopper portion. The injection needle 18d is connected to the overflow bag 13 in order to prevent the contamination of the filling apparatus inside when a labeled drug has overflowed the label vial 10.

The label vial 10 is accommodated in a vial shield 11 made of lead, and the vial shield 11 is fixed to a cartridge 12. The RI vial 1, the label vial 10 and the drain vial 16 are accommodated in respective vial shields 11 made of lead to prevent the leakage of radiation from the RI solution contained therein, to outside.

The cartridge 12 is rotated by a driving device 19 with the center of rotation fixed at a point 20, whereby the contents in the label vial 10 are stirred. Herein, "stirring" means this operation.

After the completion of the stirring, the vial shield 11 accommodating the label vial 10 comes to a standstill with its opening 22 directed obliquely upward at the side opposite to the operator, as shown in FIG. 2. In FIG. 2, the cartridge 12 is omitted.

Figure 3:
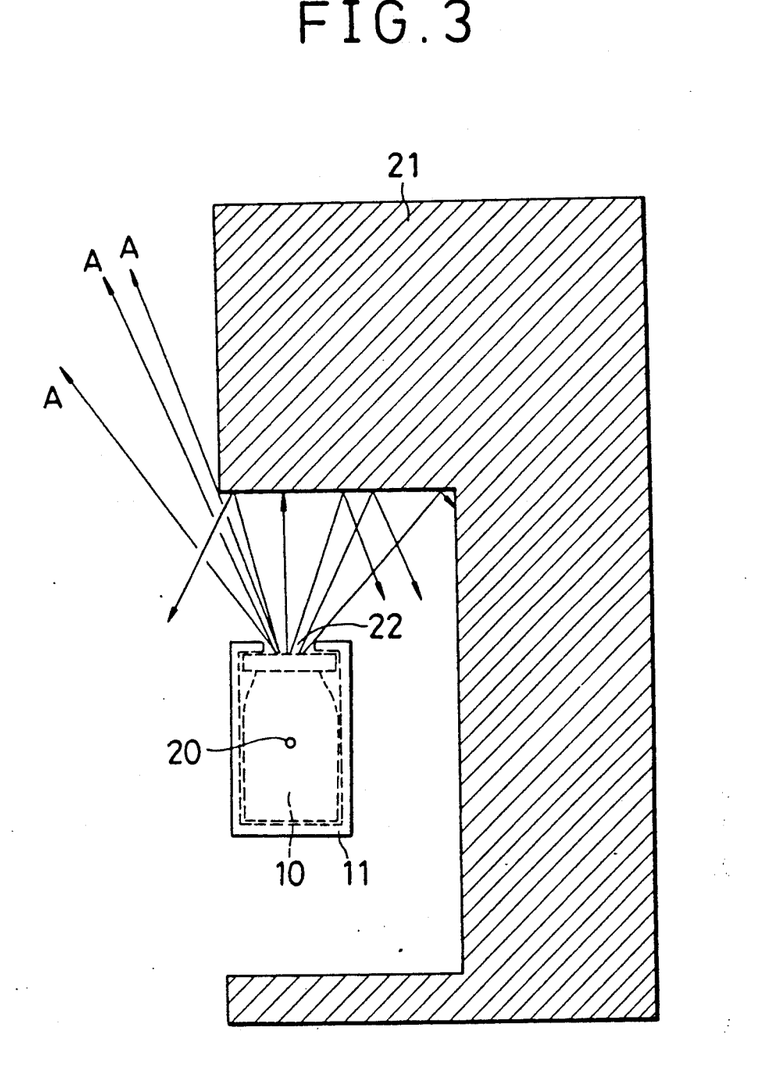
FIG. 3 is a view showing a state that a vial shield containing a label vial has come to a standstill after the completion of the stirring operation, with its opening directed upward.

In FIGS. 2 and 3, arrows A are radiations leaking from the opening 22 of the vial shield 11. It is appreciated from these drawings that in the automatic RI filling apparatus of the present invention, unlike the conventional apparatus of FIG. 3 which comes to a standstill with the opening 22 directed upright, the amount of the radiation leaking toward the operator can be reduced significantly. A casing 21 is provided in the present or conventional automatic RI filling apparatus.

The operation of the apparatus of FIG. 1 is explained.

(i) Preparation of diluted RI solution (1) The switching valves 6a, 6c, 6d, and 6e are closed by the command of the computer 14. The piston of the syringe 2 is lifted by a required stroke, whereby a required amount of RI solution is collected from the RI vial. Then, the switching valve 6b is closed, the switching valve 6c is opened, and the piston of the syringe 2 is pressed down by a required stroke, whereby the RI solution is transferred to the dilution vial 4.

(2) The switching valve 6c is closed, the switching valve 6e is opened, and a required amount of a physiological saline solution is collected from the saline vial 3. Then, the valve 6e is closed, the valve 6c is opened, and a required amount of the physiological saline solution is transferred to the dilution vial 4.

(3) The thus prepared diluted RI solution is measured for radioactive intensity by a radiation detector 15. The measured value is input into the computer 14. The computer 14 calculates the amount of the diluted RI solution to be transferred to each label vial 10, based on the above measured value as well as on the required radioactivity and volume of labeled drug, the amount of drug and the name of nuclide all input to the computer 14.

(ii) Transfer of diluted RI solution to label vial (1) In a state that, of the valves 6a to 6f, only the valve 6c is opened, the diluted RI solution of the amount calculated by the computer 14 is collected from the dilution vial 4 by the syringe 2.

(2) Then, the valves 6c, 6h and 6i are closed, the valves 6d and 6g are opened, and the piston of the syringe 2 is lowered, whereby a required amount of the diluted RI solution is provided into the label vial 10a.

(3) Thereafter, a required amount of the diluted RI solution is provided into each of the label vial 10b and the label vial 10c.

(4) The label vial 10 is rotated together with the cartridge 12 with the point 20 fixed as a center of rotation, to effect stirring.

In place of effecting stirring after providing the diluted RI solution to all the label vials, it is possible to effect stirring each time when one label vial has been provided with the diluted RI solution.

(5) After the completion of the stirring, the label vial 10 and the vial shield 11 come to a standstill with the shield opening 22 directed obliquely upward at the side opposite to the operator, as shown in FIG. 2.

Next, explanation is made on the operation of the second filling apparatus of the present invention, referring to FIG. 1.

(iii) Preparation of diluted RI solution

This is effected according to the same procedure as in the first filling apparatus.

(iv) Transfer of diluted RI solution to label vial (1) In a state that, of the valves 6a to 6f, only the valve 6c is opened, the diluted RI solution of the amount calculated by the computer 14 is collected from the dilution vial 4 by the syringe 2.

(2) Then, the valves 6c, 6h and 6i are closed, the valves 6d and 6g are opened, and the piston of the syringe 2 is lowered, whereby a required amount of the diluted RI solution is provided into the label vial 10a.

(3) The valve 6g is closed, and the cartridge 12 is lowered or the injection needles 18c and 18d are lifted to pull out the injection needles 18c and 18d from the label vial 10a.

(4) Immediately, stirring is effected to mix the contents of the label vial 10a thoroughly. The stirring is effected by, for example, rotating the cartridge 12 as indicated by an arrow b, by means of the driving device 19.

(5) The cartridge 12 is lifted or the injection needles 18c and 18d are lowered to insert these injection needles into the rubber stopper of the label vial 10a.

(6) The procedure (1) to (3) is repeated to provide the diluted RI solution into the label vial 10b.

(7) The procedure (4) is repeated to mix the contents of the label vial 10b.

(8) The procedure (5) is repeated to insert the injection needles 18c and 18d into the rubber stopper of the label vial 10b.

(9) The procedure (1) to (3) is repeated to provide a required amount of the diluted RI solution into the label vial 10c.

(10) The procedure (4) is repeated to mix the contents of the label vial 10c.

Next, explanation is made on the third filling apparatus of the present invention.

For convenience, explanation is made only on the different points from the apparatus of FIG. 1.

Figure 4:
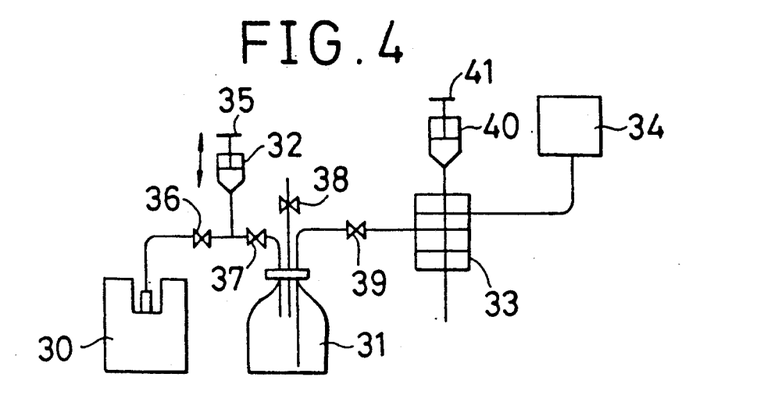
FIGS. 4–6 are each a fragmentary view showing an example of a portion of the third filling apparatus of the present invention for transferring a RI solution from a RI generator to a dilution vial.

FIG. 4 is a fragmentary view showing an example of a portion of the third filling apparatus of the present invention for transferring a RI solution from a RI generator to a dilution vial. 30 is a RI generator, 31 (4 in FIG. 1) is a dilution vial, 32 is a syringe, 33 is a manifold for conduit distribution, and 34 is a saline vial.

In the apparatus of FIG. 4, a switching valve 36 is opened, a switching valve 37 is closed, and the piston 35 of the syringe 32 is pulled by a required stroke, whereby a required amount of a RI solution is pulled into the syringe 32 from the RI generator 30. Then, the valve 36 is closed, the valve 37 is opened, and the piston 35 is pushed down to the bottom of the syringe 32, whereby a required amount of the RI solution is transferred to the dilution vial 31. The radioactive intensity of the required amount of the RI solution transferred to the dilution vial 31 is measured by the radiation detector 15 as shown in FIG. 1.

A switching valve 39 is closed and a piston 41 of a syringe 40 is pulled by a required stroke, whereby a required amount of a physiological saline solution is collected into the syringe 40 from the saline vial 34. Then, the valve 39 is opened, and the piston 41 is pushed down to the bottom of the syringe 40, whereby a required amount of the physiological saline solution is transferred to the dilution vial 31.

By operating as above, a required amount of a RI solution having an adjusted specific radioactivity is accommodated in the dilution vial 31.

The subsequent operation, i.e. the step of transferring from the dilution vial 31 (the dilution vial 4 in FIG. 1) to the label vial 10 for labeling is effected in the same procedure as in FIG. 1.

Figure 5:
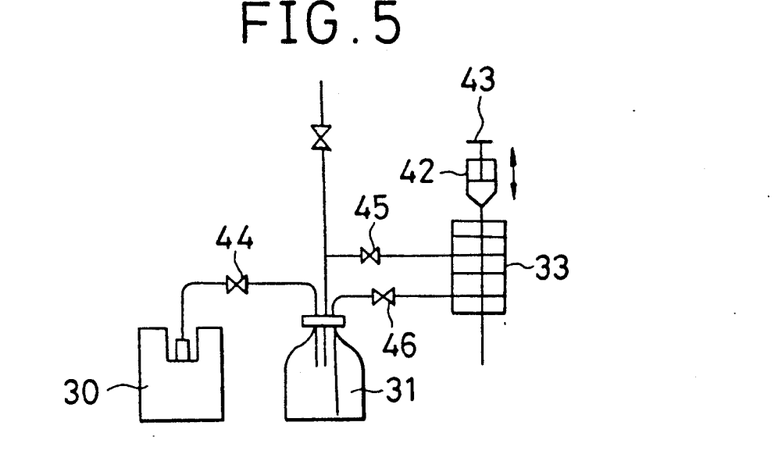

FIG. 5 is a fragmentary view showing another example of a portion of the third filling apparatus of the present invention for transferring a RI solution from a RI generator to a dilution vial. In this example, a syringe 42 performs both of (a) suction of a RI solution from a RI generator and (b) transfer from a dilution vial 31 to the label vial 10 shown in FIG. 1. In the example of FIG. 5, it is necessary that the inside of the dilution vial 31 be made into a vacuum.

Figure 6:
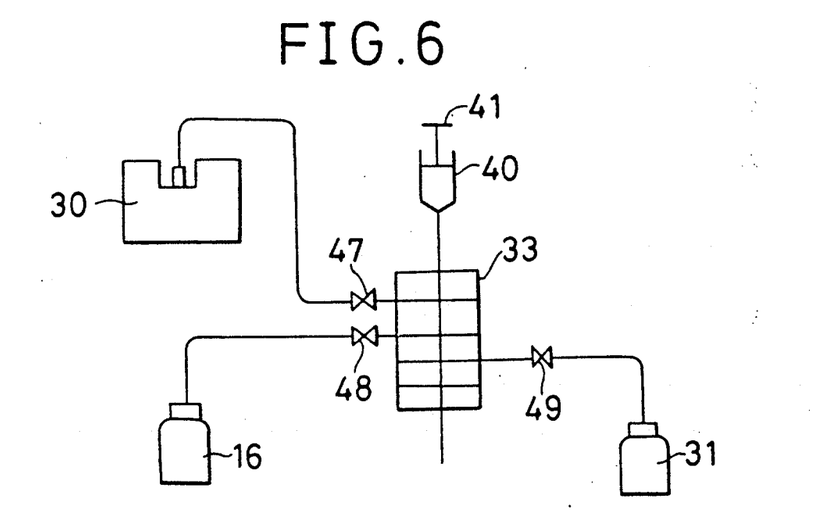

FIG. 6 shows an example of a case wherein the RI solution first collected from a RI generator 30 is discharged into a drain vial 16.

Figure 7:
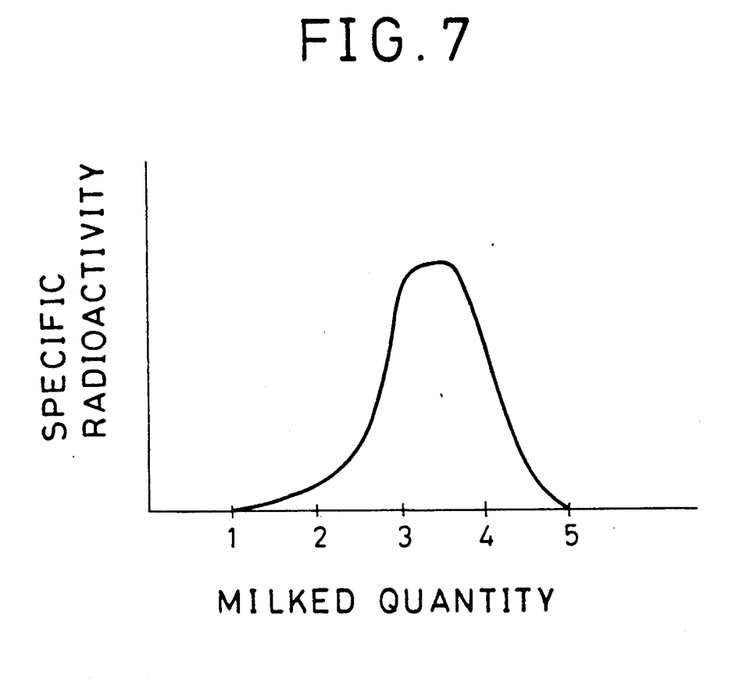
FIG. 7 is a graph showing the concentration distribution of a RI solution obtained from a RI generator by milking of RI.

The specific radioactivity of the RI solution obtained from the RI generator 30 by milking changes in the form of a mountain shape as shown in FIG. 7, with the progress of the milking. When the unit of the abscissa of FIG. 7 is taken as, for example, $cm^3$, a majority of radioactivity is contained ordinarily in the milking amount range (of the RI solution) of 2.5–4.5 $cm^3$. When a RI solution of high specific radioactivity is desired, such a RI solution can be obtained by discharging a RI solution portion of up to 2.5 $cm^3$ (the portion has a small specific radioactivity) and collecting the subsequent RI solution portion of 2.5–4.5 $cm^3$.

In FIG. 6, a switching valve 47 is opened, a required amount of a RI solution is sucked into a syringe 40, the valve 47 is closed, and a switching valve 48 is opened, whereby the RI solution of a small specific radioactivity which is first collected into the syringe 40 is discharged into the drain vial 16. The RI solution sucked into the syringe 40 in the same manner is transferred to a dilution vial 31 by opening a switching valve 49, whereby a RI solution of large specific radioactivity can be obtained.

Tc-99m has a short half life of 6 hours. Therefore, in order to obtain a RI solution of desired radioactivity or specific radioactivity, it is desirable to milk Tc 99m from the RI generator right before the preparation of a labeled drug.

The timing of administration of a labeled drug to patients is various (e.g. early morning or afternoon) depending upon the organ of patient to be examined, the number of patients, the usability of diagnostic instrument, etc. Therefore, a person who prepares a labeled drug must prepare the labeled drug so as to meet the above timing. That is, the timing of preparation of a labeled drug is dependent upon the timing of labeled drug administration to patients.

In the third filling apparatus, the computer 14 (shown in FIG. 1) controlling the entire apparatus has a conventional built in timer and is provided with an automatic operational program for periodically reading time from the timer and automatically effecting collection, transfer and labeling at designated timings.

Figure 8:
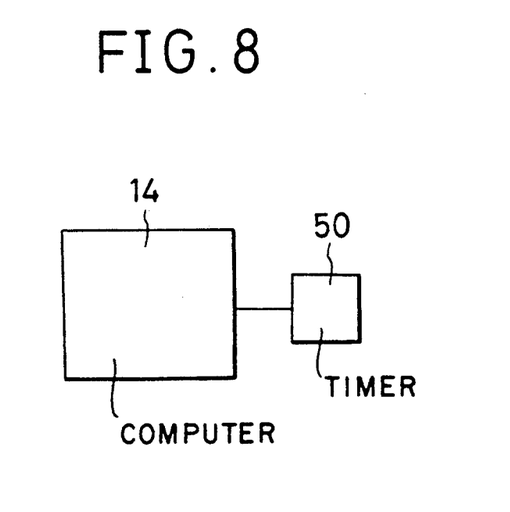
FIG. 8 is a fragmentary view showing a portion where a timer is connected to a computer.

In an example of the above automatic operational program, a conventional timer 50 is connected to the computer 14 as shown in FIG. 8; a time-up signal issued by the timer 50 after the lapse of a designated time period is detected by the computer 14; thereby, collection, transfer and labeling are effected automatically.

Thus, by making in advance the preparations necessary for collection, transfer and labeling, the operator of the filling apparatus can allow the apparatus to automatically perform its operation at a designated time or after the lapse of a designated time period. As a result, the operator need not be restricted by the timing of labeled drug administration to patients.

Next, the operation of the third filling apparatus is explained in order.

I. The cartridge 12 accommodating a given number of the label vials 10 is set in the filling apparatus.

The dilution vial 4 and the drain vial 16 are set in respective designated positions.

II. The tube unit is set in the filling apparatus.

The injection needles connected to the tube unit are inserted into the label vial 10, the dilution vial 4 and the drain vial 16, respectively.

III. The data necessary for filling operation is input into the computer 14.

The desired radioactivity and volume of each label vial 10 are input.

Use or no use of a timer is input. In case of use, the start time is input.

A. After the inputting, the computer 14 calculates the specific radioactivity and volume of the RI solution to be transferred to each label vial 10.

IV. The saline vial 34 is set.

V. The tube 5 of the tube unit is connected to the RI generator 30.

VI. Start of transfer

The given button of the computer 14 is pressed to allow the filling apparatus to start the following operation.

(1) When no use of a timer has been input in III above, the following items A to H are started immediately.

(2) When use of a timer has been input in III above, the following items A to H are started when the designated time has come.

A. The original RI solution is sucked from the RI generator 30 by the syringe 32 and transferred to the dilution vial 31.

B. The volume of the original RI solution is calculated from the stroke of the syringe 32.

C. The radioactive intensity of the original RI solution is measured.

D. The original RI solution in the dilution vial 31 is diluted with a physiological saline solution so as to give a diluted RI solution of the highest specific radioactivity required in the label vial 10.

E. The diluted RI solution is metered and transferred to the first label vial 10.

F. The procedure of E above is repeated to transfer the diluted RI solution to other label vials 10.

When there is required a diluted RI solution of a lower specific radioactivity, the diluted RI solution is diluted to a lower concentration with the physiological saline solution, metered and transferred to the label vial 10.

G. When the transfer is complete, the inside of the tube 5 connecting to each label vial 10 is sucked by the syringe 40 to transfer the residual solution in each injection needle to the drain vial 16.

H. The indication of the completion of filling operation is given to the computer 14.

The details of filling operation are printed by a printer when the filling operation is over.

When the portion of the original RI solution of small specific radioactivity is discarded and the portion of the original RI solution of higher specific radioactivity is used, the filling operation is different from the above only in the following.

A. In III above (inputting of the data necessary for filling operation to the computer 14), there is also input the volume of the original RI solution to be discarded.

B. Before the action of VI-A, the RI solution from the RI generator 30 is sucked by the syringe 32 and then discharged into the drain vial 16. (The subsequent procedure is same as VI.)

Next, an explanation is given on the fourth filling apparatus of the present invention referring to FIGS. 9-12.

Figure 9:
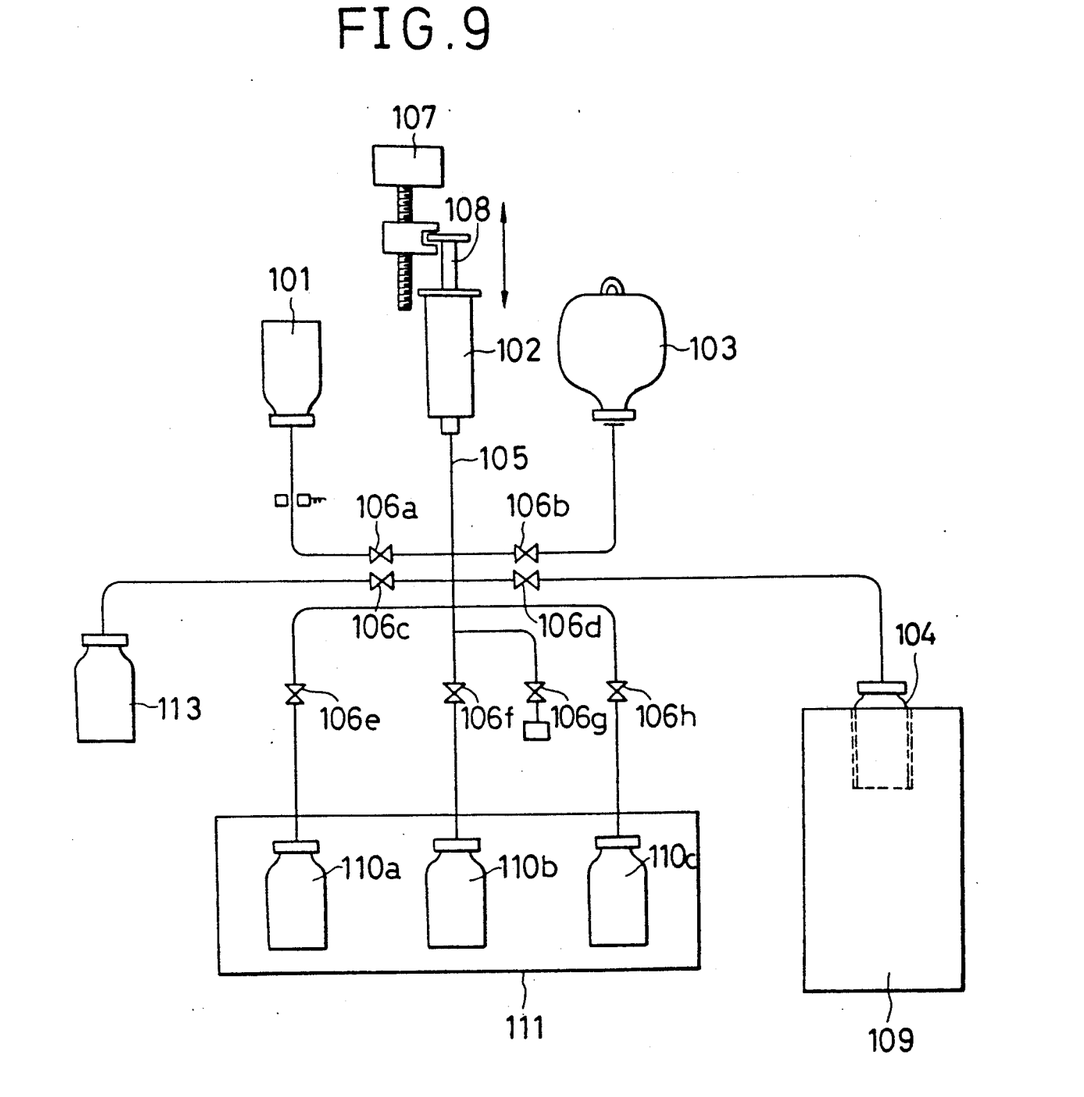
FIG. 9 is a schematic view showing one embodiment of the fourth filling apparatus of the present invention.

In the automatic RI filling apparatus of FIG. 9, 101 is a RI vial containing an original RI solution; 102 is a syringe which is a volume meter and is constituted by, for example, a cylinder and a piston; 103 is a saline vial containing a physiological saline solution; 104 is dilution vial to which the original RI solution or the physiological saline solution is to be transferred; and 110 is a label vial to which a required amount of the original RI solution or the physiological saline solution is to be transferred. The RI vial 101, the syringe 102, the saline vial 103, the dilution vial 104 and the label vial 110 are connected to each other by a tube 105. Switching valves 106a to 106h are provided in the middle of the tube 105. The piston 108 of the syringe 102 can make a straight line reciprocal movement by the assistance of a driving device 107. The radioactive intensity in the dilution vial 104 is measured by a radiation detector 109.

The label vials 110a to 110c to which a given amount of the RI solution or the physiological saline solution is to be transferred are contained in respective vial shields (not shown) made of lead, and the vial shields are accommodated in a cartridge 111 which is a portable frame.

Figure 10:
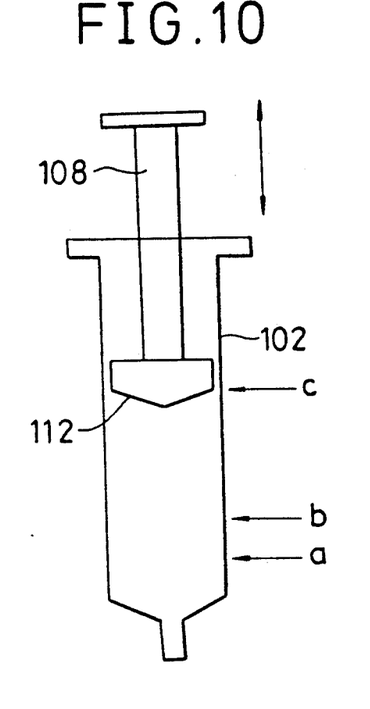
FIG. 10 is a sectional view showing an outline of a syringe.

In the thus constituted apparatus, before the start of the operation of the apparatus; the dilution vial 104 is empty; the piston 108 of the syringe 102 is inserted down to a point a which is a starting point of the operation of the piston 108, as shown in FIG. 10; and the switching valves 106a to 106h are all closed.

At the start of the operation of the apparatus, the switching valve 106g for air is opened; the piston 108 is pulled by the driving device 107 from the point a to a point b (a completion point of air suction), as shown in FIG. 10; thereby there is sucked into the syringe 102 air of an amount corresponding to the maximum internal volume of the tube 105 (the internal volume of the tube 105 differs by the transfer route of the tube 105). Then, the valve 106g for air is closed and the valve 106a is opened; the piston 108 is pulled by the driving device 107 from the point b to a point c (a completion point of suction of solution); thereby, a required amount of the original RI solution is collected into the syringe 102 from the RI vial 101. Next, the valve 106a is closed; the valve 106d is opened; the piston 108 is pressed down by the driving device 107 to the point a of the syringe 102 using the air as a buffer material; thereby, a required amount of the original RI solution is transferred to the dilution vial 104.

Thus, a given amount of air is sucked into the syringe 102; then, the original RI solution is collected into the syringe 102; thereafter, the piston is pressed down using the air as a buffer material to transfer the original RI solution to the dilution vial 104. Therefore, the front end 112 of the piston 108 makes no contact with the original RI solution. This collection and transfer of the RI solution into and from the syringe 102 is effected in the same manner also in the next and later operations. Consequently, there is no fear that the radioactivity of the RI solution to be transferred to the dilution vial and further to the label vial becomes inaccurate.

In transferring the RI solution in the syringe 102 to the dilution vial 104, it is preferable to discharge the solution in the tube at $V_1 > V_2$ using air as a buffer material when the $V_1$ is defined as a flow speed in the tube 105 when the solution is in the syringe 102 and $V_2$ is defined as a flow speed in the tube 105 when the solution in the syringe 102 has been completely discharged.

That is, the transfer of the solution to the syringe 102 is complete in a shorter time as the flow speed is faster. However, too fast a speed causes a pressure increase inside the tube 105 and may cause solution leakage at tube joints, etc. Hence, an appropriate speed is required to keep the pressure increase which is effected by such parameters as the inside diameter of the tube 105, the flow speed and the solution viscosity, within a pressure level allowed for the tube. Such a speed is defined as $V_1$.

In discharging the solution in the tube 105, the flow speed is required to be small in order to minimize the adhesion of the solution to the inner wall of the tube 105. Too large a speed allows air to pass through the tube and consequently many solution droplets remain on the inner wall of the tube. Such a speed is defined as $V_2$.

Therefore, it is preferable to discharge the solution using air as a buffer material so that the flow speed in the tube 105 satisfies a requirement of $V_1 > V_2$. According to various experiments made by the present inventor, the appropriate $V_2$ for a physiological saline solution was 0.1-25 mm/sec when there was used a soft polyvinyl chloride tube of 0.5-1.5 mm in inside diameter.

The $V_1$ is determined by the constitution of conduit (e.g. tube length, inside diameter and length of injection needle provided at the front end of tube) and cannot be specified numerically. The appropriate $V_1$ was 100-3,000 mm/sec when the inside diameter of tube was 0.5-1.5 mm, according to an example wherein an injection needle of 0.6 mm in inside diameter and 100 mm in length was attached to the front end of a tube 105 of 500 mm in length.

In sucking a solution into the syringe 102 in a state that a given amount of air is contained in the syringe 2, it is preferable to suck the solution into the syringe 2 at $V_3 < V_4$ when $V_3$ (lower speed) is defined as a solution speed in the tube 105 from the start of suction up to a time when the solution at the bottom reaches a predetermined height and $V_4$ (higher speed) is defined as a solution speed in the tube after said time.

Figure 11A:
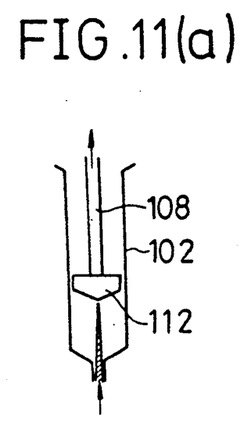
Figure 11B:
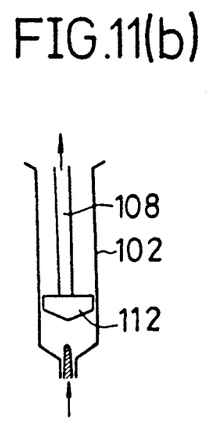
Figure 11C:
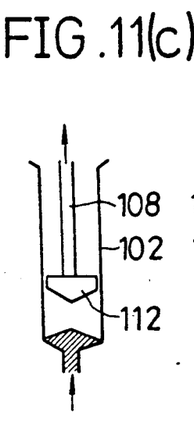
Figure 11D:
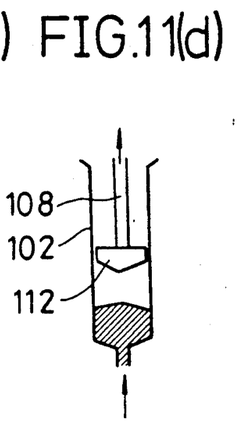

The suction of a solution into the syringe 102 is complete in a shorter time as the solution speed is faster. However, when suction is started at too fast a speed in a state that air is contained in the syringe 102 as shown in FIG. 11, the solution is sucked into the syringe 102 in a jet form as shown in FIG. 11 (a), causing adhesion of solution droplets to the front end 112 of the syringe piston 108.

Hence, in the present invention, as shown in FIGS. 11 (b) and (c), suction is effected slowly at $V_3$ (lower speed) until the solution is stored at the bottom portion of the syringe 102 and, after the solution has reached a given height, at a higher speed ($V_4$); thereby, there occurs no adhesion of solution droplets to the syringe front end and the suction time is made as short as possible.

The radioactive intensity of a required amount of the original RI solution transferred to the dilution vial 104 is measured by the radiation detector 109.

In another example, when a RI solution of known volume and known radioactivity is in the dilution vial 104 and it is desired to lower the specific radioactivity by dilution, the valve 106b is opened and the piston 108 is pulled by a required stroke by the driving device 107, whereby a required amount of the physiological saline solution is collected into the syringe 102 from the saline vial 103.

Next, the valve 106b is closed, the valve 106d is opened, and the piston 108 is pressed down to the point a of the syringe 102, whereby a required amount of the physiological saline solution is transferred to the dilution vial 104 and the RI solution in the dilution vial 104 is diluted to obtain a diluted RI solution of a desired lower specific radioactivity.

The label vials 110a to 110c containing a drug mixed with a required amount of the RI solution or the physiological saline solution are accommodated in the label vial cartridge 111 which is a portable frame.

When the transfer to the label vials 110a to 110c is complete, the RI solution remaining in the dilution vial 104 and the tube 105 is transferred to the drain vial 113 via the syringe 102. It is specifically effected by sucking into the syringe 102 air of an amount of at least equivalent to the inner volume of the tube 105 and then pressing down the piston 108 using the air as a buffer material to discharge the residual solution in the dilution vial 104 or the tube 105 into the drain vial 113.

Results of actual operation of the filling apparatuses of the present invention are shown below.

EXAMPLE 1

Labeling of drags was effected using the second filling apparatus of the present invention.

Labeling of MDP (methylene diphosphonic acid), phytic acid and albumin with Tc-99m (technetium-99m) was effected using the second filling apparatus.

MDP (methylene diphosphonic acid), phytic acid and albumin were placed in label vials 10a, 10b and 10c, respectively.

As a RI solution, there was used a solution of Tc-99m (technetium-99m).

By effecting the operation of the above (iv) (1)-(8), a diluted RI solution was transferred to one label vial and immediately stirring was effected; then, the diluted RI solution was transferred to a second label vial.

The thus prepared labeled drugs were measured for labeling efficiency. The results are shown in Table 1.

COMPARATIVE EXAMPLE

Labeling of drugs was effected using a conventional RI filling apparatus.

MDP (methylene diphosphonic acid), phytic acid and albumin were placed in label vials 10a, 10b and 10c, respectively.

As a RI solution, there was used a solution of Tc-99m (technetium 99m).

A diluted RI solution was transferred to the label vials 10a to 10c and then stirring was effected.

The thus prepared labeled drugs were measured for labeling efficiency. The results are shown in Table 1.

TABLE 1

| Labeling efficiency of drugs in labeled vials | | | |
|---|---|---|---|
| Labeled vial | 10a | 10b | 10c |
| Example 1 | 99% | 99% | 100% |
| Comparative Example | 97% | 93% | 98% |

Label vial 10a contained methylene diphosphonic acid
Label vial 10b contained phytic acid.
Label vial 10c contained albumin.

EXAMPLE 2

By using the apparatus of FIG. 9, operating the valves in accordance with the procedure as explained above, and employing the conditions cf a syringe stroke of 56.6 mm, a syringe volume of about 1 cc, a tube length of 1 m and water (as a liquid to be passed through the apparatus), water was transferred from the dilution vial 104 to the label vial 110a at various syringe piston speeds, and the forms of water remaining in the tube, the joints and the syringe were visualized to investigate the relationship between the syringe piston speed, the water speed in the tube and the water form in the tube.

The results are shown in Table 2. Consequently, it was found that a lower syringe speed gives a better "inside tube" condition.

TABLE 2

| Syringe piston speed (mm/s) | Water speed in tube (mm/s) | Water form in tube |
|---|---|---|
| 1.0 | 22.5 | ⊙ |
| 1.3 | 29.2 | ○ |
| 1.7 | 38.2 | ○ |
| 2.0 | 45.0 | Δ |
| 5.0 | 112.4 | Δ |
| 10.0 | 224.9 | X |
| 20.0 | 449.8 | X |

Figure 12:
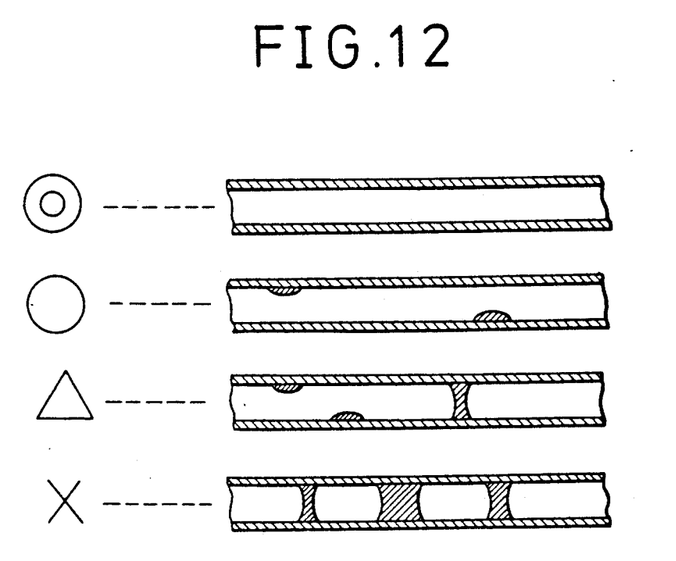
FIG. 12 is a view showing forms of a fluid remaining in a tube.

In Table 2, ⊙, ○, Δ and X all showing the water forms in tube refer to the conditions shown in FIG. 12.

What is claimed is:

1. An automatic radioisotope filling apparatus comprising:
   a radioisotope vial containing a radioisotope solution;
   a saline vial containing a physiological saline solution;
   a plurality of label vials containing a drug into which a predetermined amount of the radioisotope solution or the physiological saline solution is to be provided;
   a plurality of vial shields, an opening of each vial shield, accommodating each label vial, is directed obliquely upward at a side of the vial shield which is opposite an operator when stirring of each label vial has been completed; and
   withdraw and transfer means for withdrawing said radioisotope solution and physiological saline solution and for transferring said solutions to said label vials.

2. An automatic radioisotope filling apparatus comprising:
   a radioisotope vial containing a radioisotope solution;
   a saline vial containing a physiological saline solution;
   a dilution vial into which a predetermined amount of the radioisotope solution and a predetermined amount of the physiological saline solution are provided to prepare a diluted radioisotope solution;
   a radiation detector for measuring the radioactive intensity of the solution in the dilution vial;
   a plurality of label vials containing a drug to be labeled; and
   withdraw and transfer means for withdrawing and transferring said solutions, wherein the diluted radioisotope solution preparation in the dilution vial is provided into each of the label vials containing said drug, prepared as a labeled drug, and wherein each label vial is provided with a predetermined amount of the diluted radioisotope solution and means for immediately subjecting a label vial to stirring before a next label vial is subjected to a same procedure.

3. An automatic radioisotope filling apparatus according to claim 2, wherein the stirring is effected by rotating each label vial about a lateral axis of each label vial.

4. An automatic radioisotope filling apparatus comprising:
   a radioisotope generator for milking a radioisotope to produce a radioisotope solution;
   a saline vial containing a physiological saline solution;
   a plurality of label vials containing a drug into which a predetermined amount of the radioisotope solution or the physiological saline solution is to be provided;
   a metering and transfer means for withdrawing and transferring a predetermined amount of the radioisotope solution from the radioisotope generator by suction;
   a dilution vial into which a predetermined amount of the radioisotope solution and a predetermined amount of the physiological saline solution are provided to prepare a diluted radioisotope solution; and
   a radiation detector for measuring radioactive intensity of the radioisotope solution transferred to the dilution vial,
   wherein specific radioactivity of the radioisotope solution transferred to the dilution vial is calculated based on volume of the radioisotope solution transferred to the dilution vial, the radioactive intensity of the radioisotope solution measured by the radiation detector, an amount of drug needed and a name of a nuclide.

5. An automatic radioisotope filling apparatus according to claim 4, further comprising:
   a drain vial for discharging a given amount of the radioisotope solution supplied from the radioisotope generator, wherein said given amount of the radioisotope solution supplied from the radioisotope generator is first discharged into the drain vial and then a desired amount of the radioisotope solution is metered and transferred to the dilution vial.

6. An automatic radioisotope filling apparatus according to claim 4, further comprising:
   an operation control device including a timer, wherein an operation is started at a specified time or after a lapse of a specified time period.

7. An automatic radioisotope filling apparatus comprising:
   a radioisotope vial containing a radioisotope solution, or a radioisotope generator for milking a radioisotope to produce a radioisotope solution;
   a saline vial containing a physiological saline solution;
   a syringe for withdrawing a predetermined amount of the radioisotope solution or the physiological saline solution by suction;
   a dilution vial into which a measured amount of the radioisotope solution or a measured amount of the physiological saline solution is to be provided;
   a plurality of label vials containing a drug into which a predetermined amount of the radioisotope solution or a predetermined amount of the physiological saline solution is to be provided; and
   a tube connecting the syringe, the vials and the generator,
   wherein in discharging the solution remaining in the tube, an amount of air, at least equivalent to the internal volume of a discharging section of the tube, is sucked into the syringe and then the solution remaining in the tube is discharged using the air as a buffer material.

8. An automatic radioisotope filling apparatus according to claim 7, wherein in sucking the radioisotope solution or the physiological saline solution into the syringe and discharging the solution from the syringe, the position of the syringe piston at a start of suctioning of the solution and at completion of discharging of the solution is set at a position above the syringe bottom with a certain amount of air filled up to said position.

9. An automatic radioisotope filling apparatus according to claim 7, further comprising a control means for controlling discharge of the syringe wherein in discharging the solution in the syringe, the syringe discharging the solution in the tube at a flow speed in the tube, when the solution is in the syringe, which is greater than a flow speed in the tube when the solution in the tube has been completely discharged using air as a buffer material.

10. An automatic radioisotope filling apparatus according to claim 7, further comprising a control means for controlling sucking of the syringe wherein in sucking the solution into the syringe in a state that a predetermined amount of air is in the syringe, the syringe sucking the solution into the syringe at a solution speed in the tube, from the start of suction up to a time when the solution at the syringe bottom reaches a predetermined height, which is greater than a solution speed in the tube after said time.

* * * * *